(12) United States Patent
Fan et al.

(10) Patent No.: US 7,758,895 B2
(45) Date of Patent: Jul. 20, 2010

(54) METHODS FOR PURIFYING INSOLUBLE BONE GELATIN

(75) Inventors: Ying Fan, City Beach (AU); Ming Hao Zheng, City Beach (AU); David Wood, City Beach (AU)

(73) Assignee: Perth Bone and Tissue Bank, Nedlands (AU)

( * ) Notice: Subject to any disclaimer, the term of this patent is extended or adjusted under 35 U.S.C. 154(b) by 1610 days.

(21) Appl. No.: 10/234,618

(22) Filed: Sep. 4, 2002

(65) Prior Publication Data

US 2003/0065392 A1    Apr. 3, 2003

Related U.S. Application Data

(60) Provisional application No. 60/317,097, filed on Sep. 4, 2001.

(51) Int. Cl.
*A61K 35/32* (2006.01)

(52) U.S. Cl. ............... 424/549; 514/2; 514/21; 530/354; 530/355; 530/840; 424/422; 424/520; 424/548

(58) Field of Classification Search ........... 424/549
See application file for complete search history.

(56) References Cited

U.S. PATENT DOCUMENTS

| | | | |
|---|---|---|---|
| 4,294,753 A | | 10/1981 | Urist |
| 4,619,989 A | | 10/1986 | Urist |
| 4,804,744 A | * | 2/1989 | Sen ............................ 530/350 |
| 4,990,333 A | * | 2/1991 | Lane et al. ................... 424/551 |
| 5,918,821 A | * | 7/1999 | Grooms et al. ................ 241/27 |
| 6,180,606 B1 | | 1/2001 | Chen et al. |
| 2001/0014831 A1 | * | 8/2001 | Scarborough ............ 623/23.51 |

OTHER PUBLICATIONS

Urist et al, Clinical Orthopaedics and Related Research, 1995, vol. 313, pp. 120-128.*
Russell et al, "Clinical Utility of Demineralized Bone Matrix for Osseous Defects, Arthrodesis, and Reconstruction: Impact of Processing Techniques and Study Methodology" Orthopedics (May 1999), vol. 22, No. 5, pp. 524-531.*

Feng, Li, et al., "The Clinical Application of Human Bone Matrix Gelatin," Journal of Tongji Medical University 15 (2), pp. 90-94,1995, Wuhan 430030.
Gie, G.A., et al., "Contained Morselized Allograft in Revision Total Hip Arthroplasty," The Orthopaedic Clinics of North American V. 24, No. 4, pp. 717-725, Oct. 1993.
Iwata, Hisashi, et al., "Chemosterilized Autolyzed Antigen-Extracted Allogeneic (AAA) Bone Matrix Gelatin for Repair of Defects from Excision of Benign Bone Tumors," Clinical Orthopaedics and Related Research, No. 154, pp. 150-155, Jan.-Feb. 1981.
Iwata, Hisashi, et al., "Demineralized Bone Matrix and Native Bone Morphogenetic Protein in Orthopaedic Surgery," Clinical Orthopaedics and Related Research, No. 395, pp. 99-109, Feb. 2002.
Lindholm, T. Sam, et al., "Extraskeletal and Intraskeletal New Bone Formation Induced by Demineralized Bone Matrix Combined with Bone Marrow Cells," Clinical Orthopaedics and Related Research, No. 171, pp. 251-255, Nov.-Dec. 1982.
Nogami, H., et al., "Transmembrane Bone Matrix Gelatin-Induced Differentiation of Bone," Calcified Tissue Research, V 19, No. 2, pp. 153-163, 1975.
Urist, M.R., et al., "Bone Morphogenesis in Implants of Insoluble Bone Gelatin," National Academy of Sciences of the USA, V. 70, No. 9, pp. 3511-3515, Sep. 1973.
Urist, M.R., "A Morphogenetic Matrix for Differentiation of Bone Tissue," Calcified Tissue Research, Supplement to vol. 4, pp. 98-101, Mar. 1970.
Wlodarski, K.H., "Heterotopic Bone Marrow Formation in Xenogeneic Implants of Insoluble Bone Matrix Gelatin, " Clinical Orthopaedics and Related Research, No. 171, pp. 210-212, Nov.-Dec.. 1982.
Xiaobo, H.U., et al., "Experimental and Clinical Investigations of Human Insoluble Bone Matrix Gelatin, "Clinical Orthopaedics and Related Research, V. 293, pp. 360-365, Aug. 1993.
Zheng, M.H., et al., What's New in the Role of Cytokines on Osteoblast Proliferation and Differentiation? Pathol. Res. Pract. 188, 1104-1112, 1992.

* cited by examiner

*Primary Examiner*—Allison M Ford
(74) *Attorney, Agent, or Firm*—Adam W. Bell; Matthew Kaser; Stuart Boyer

(57) ABSTRACT

The present invention provides methods for purifying insoluble bone gelatin and uses for insoluble bone gelatin. The process for isolating insoluble bone gelatin from bone tissue includes grinding the bone tissue into bone powder; washing the bone powder with saline; demineralizing the bone tissue; contacting the bone powder with a neutral salt; and contacting the bone powder with a stabilizer. The present invention also discloses an insoluble bone gelatin including about 10 percent growth factor. Insoluble bone gelatin is useful, for example, in preparing impaction bone grafts.

16 Claims, No Drawings

METHODS FOR PURIFYING INSOLUBLE BONE GELATIN

CROSS-REFERENCE TO RELATED APPLICATIONS

The application claims priority to U.S. Provisional Application No. 60/317,097, filed Sep. 4, 2001.

FIELD OF THE INVENTION

The present invention relates to methods for isolation and purification of Insoluble Bone Gelatin (ISBG) and the application of ISBG produced by the present invention, for example, for impaction bone grafting, non-union fracture and dental conditions.

BACKGROUND OF THE INVENTION

With the exception of blood, bone is the most frequently transplanted tissue in humans. With an aging population and with an increasing number of younger and more active patients undergoing, for example, hip replacement, revision surgery is often required. Currently, fresh frozen donor bone is the most effective graft material available for difficult clinical situations. Although bone transplantation has been used as the standard approach for reconstruction following excision of diseased bone, some problems remain unsolved. Among these, non-union fracture and loosening are major problems responsible for the failure of operations (especially for more extensive operations or after multiple operations), due to poor incorporation of allografts into host bone.

Bone formation in adult humans is a complex and closely regulated process. All bone is remodeled by the coordinated actions of bone resorbing (osteoclasts) and bone forming (osteoblasts) cells that are under the regulatory control of local cytokines generated in the environment of the remodeling cells. These local factors are comprised of peptides and nonpeptides. These factors are often incorporated into non-collagenous protein of bone matrix, released in an active form when bone is remodeled. Complex interactions between these factors and their target cells are responsible for the normal delicate balance between bone resorption and bone formation.

Unlike most other organ systems, the specific cellular components of bone only account for a minor portion of tissue weight. The major component of bone is matrix, which accounts for 90-95% of the tissue weight. Bone matrix includes mineral phases and protein phases, which are portioned 60-65% and 40-35%, respectively, of non-cellular bone weight. The non-collagenous proteins are heterogeneous in origin and some appear to be produced by bone cells while others are incorporated from or are concentrated from serum. The non-collagenous proteins are laid down into bone matrix by binding to the mineral phase, collagen or other matrix proteins.

There are two fractions of non-collagenous bone proteins—soluble and insoluble non-collagenous bone proteins. The fraction of insoluble non-collagenous bone proteins consist of bone growth factors—the growth factor 'cocktail', which is responsible for regulating bone formation. In the 1970's, M. Urist established procedures to isolate soluble and insoluble bone morphogenetic proteins from animal bones (for example, as described in "Bone morphogenesis in implants of insoluble bone gelatin." Urist M R, Iwata H, Ceccoth P L, Doriman R L, Boyd S D, McDowell R M and Chien C. Proc Natl Acad Sci USA 1973:351 1-351 5, hereby incorporated by reference in its entirety (the Urist 1973 article). The method taught in Urist begins with crushed bone, and does not have a pre-washing step. A chloroform-methanol extraction is performed to remove blood, cells, and other debris from the bone. The method also includes a treatment step with lithium chloride, and treatment with HCl, $CaCl_2$, and EDTA at 2.degree. C. The duration of the process is about 3.5 days, and the resulting ISBG contains BMP-2 only.

Bone morphogenetic activities were observed in implants of insoluble bone gelatin in several animal models described by Urist and other researchers including the present inventors. It has now been well accepted that bone gelatin can induce bone formation and control bone morphogenetic reaction.

It is believed that Gie et al. was first to describe the use of impaction bone allografting in revision surgery (for example, as described in "Contained morselized allograft in revision total hip arthroplasty." Gie G A, Linder L, Ling R S, Simon J P, Slooff T J, Timperley A J Orthop Clin North Am 1993 24:717-725, hereby incorporated by reference in its entirety) and this technique has been used widely since then. Even with the improvement of techniques and materials used in this field, loosening still remains a big problem.

SUMMARY OF THE INVENTION

The present invention discloses methods for isolating and purifying insoluble bone gelatin (ISBG). The present invention teaches isolation and purification of ISBG and its clinical application, for example, in impaction bone grafts and non-union fracture healing.

In general terms, the invention involves methods for preparing bone powder and, isolating and purifying ISBG, and the resulting purified ISBG and use of it in, for example, impaction bone grafts and non-union fracture healing.

An insoluble bone gelatin including about 10 percent growth factor is also included in the present invention. In one embodiment of the present invention, the growth factors are BMP-2, FGF, TGF-beta, and IGF, or any combination thereof.

DETAILED DESCRIPTION OF THE INVENTION

To meet clinical requirements, Perth Bone & Tissue Bank has recently established a primary technique of purification of ISBG as described herein. The ISBG containing about 10 percent by weight of non-collagenous proteins represents a growth factor "cocktail" is believed to enhance new bone formation and could also provide mechanical stability when mixed with milled bone (Zheng M H, Wood D J, Papadimitriou J M, "What's new in the role of cytokines on osteoblast differentiation?" Pathol. Res. Pract. 188:1104-1112). Consequently, we purified ISBG and used it with milled bone to induce bone formation and mechanical stability suitable for impaction grafts.

In one embodiment, the present technique for purification of ISBG differs from the prior art in terms of preparation of bone powder (for example, as described below), the pretreatment procedure, temperature and the chemicals used.

A method for isolating bone gelatin was established by Urist (for example, in U.S. Pat. No. 4,294,753, hereby incorporated by reference in its entirety).

In an embodiment of the present invention, a novel ISBG containing one or more of BMP-2, FGF, TGF-beta, IGF, and IGF binding protein, or any combination thereof, is produced by milling bone powder to up to about 1.0 millimeter particles and pre-washing the bone powder with saline at 35-55° C., preferably 40-45° C. for 5 minutes. The milled bone powder is treated with HCl, $CaCl_2$, and EDTA at 4° C., as described in detail below, and the entire procedure takes approximately 48 hours. No chloroform or methanol extraction process is used, and no lithium chloride solution is used in the process for obtaining the novel ISBG of this particular embodiment. The ISBG produced is useful in preparing impaction bone grafts.

In one embodiment, the present invention includes the steps of screening and testing human bones to determine suitability for human transplantation, preparing bone powder (preferably having a particle size up to 1.0 millimeter, more preferably 0.5-1.0 millimeter), isolating and purifying insoluble bone gelatin from the bone powder, and using the purified insoluble bone gelatin, for example, for impaction bone grafting, non-union fracture, and dental use.

In one embodiment of the isolation and purification procedure according to the present invention, bone powder prepared according to the present invention was demineralized using an acid such as hydrochloric acid or acetic acid, then treated with a neutralizing salt such as calcium chloride or calcium phosphate, and then treated with a stabilizer such as ethylene diamine tetraacetic acid (EDTA). The resulting gelatin was then treated with sterilized water.

Three protocols (described below) were designed and tested based on the concept that ISBG contains a growth factor "cocktail" that includes one or more of BMP-2, FGF, TGF-beta, IGF, and IGF binding proteins, and provides mechanical stability in impaction bone grafts. Protocol 1 is according to the Urist 1973 article. Protocols 2 and 3 are according to the present invention.

Protocol 1

Bone powders without any pre-preparation step were subjected to the following procedure for ISBG extraction.
Step 1 chloroform and methanol (1:1 ratio) for 4 hours at 25° C.;
Step 2 0.6 N HCl for 24 hours at 4° C.;
Step 3 2.0 M $CaCl_2$ for 24 hours at 4° C.;
Step 4 0.5 M EDTA for 24 hours at 4° C.;
Step 5 8.0 M LiCl for 4 hours at 4° C.; and
Step 6 sterilized $H_2O$ for 4 hours at 55° C.

Protocol 2

Bone powders prepared by the method described below were subjected to the following procedure for ISBG extraction.
Step 1 0.6 N HCl up to 24 hours at 4° C.;
Step 2 2.0 M $CaCl_2$ up to 24 hours at 4° C.;
Step 3 0.5 M EDTA up to 24 hours at 4° C.;
Step 4 8.0 M LiCl for 4 hours at 4° C.; and
Step 5 sterilized $H_2O$ for 4 hours at 55° C.

Protocol 3

Bone powders prepared by the method described below were subjected to the following procedure for ISBG extraction.
Step 1 0.6 N HCl up to 24 hours at 4° C.;
Step 2 2.0 M $CaCl_2$ up to 24 hours at 4° C.;
Step 3 0.5 M EDTA for 4 hours at 4° C.; and
Step 4 sterilized $H_2O$ for 4 hours at 55° C.

Instead of using chloroform and methanol solution as described by Urist, a washing procedure was developed to remove lipids and bone marrow cells in the tissue for Protocols 2 and 3 according to the present invention. In the step prior to treatment with HCl, the bone powder was washed with normal saline at 40-45° C. for 5 minutes. Using this procedure, 80% of lipids and bone marrow cells were removed at the end of washing. The bone powder rinsed with saline appeared to be clear, moist and not overly dry as is bone powder treated with a solution of chloroform and methanol.

To eliminate non-crucial chemicals, a series of experiments was conducted to examine if the use of solutions of chloroform and methanol, and lithium chloride (LiCl) are necessary for isolating and purifying ISBG. Based on the results of rat models, it was found that neither a solution of chloroform and methanol, nor a solution of LiCl is essential to produce ISBG that is suitable for induction of bone formation. By eliminating one or both of these chemicals from the isolation and purification procedure, the duration of ISBG extraction is reduced by up to approximately one-half according to the present invention.

The present invention provides very promising results to meet clinical requirements, such as osteoinductive activities and mechanical stability for impaction bone grafts. Indeed, there was no significant difference between protocols 2 & 3 as to the degree of new bone formation produced. An embodiment as described in Protocol 3 is preferable from an economic standpoint as this protocol includes fewer steps and chemicals and provides a desirable product. No adverse effects were observed using this protocol.

In one embodiment, using the protocol 3 according to the present invention, the extraction period was reduced from 3.5 days to about 2 days, and produced an ISBG material having potent osteoinductive activity as evidenced in rat models in which bone formation was observed after the implantation of ISBG. Mechanical stability in impaction bone grafts was also observed, and is thought to be related to the osteoinductivity of the ISBG. Moreover, an injectable ISBG material can be generated by using the ISBG produced according to the present invention with any acceptable pharmaceutical carriers. In one embodiment, 1% alginate gel with distilled water can be used as a pharmaceutical carrier.

In short, the ISBG isolated and purified according to the present invention has preferred biological properties, such as osteoinductivity, and mechanical stability. It will provide exceptional benefits for example, for impaction bone graft, non-union fracture and dental implantation. The results provided herein regarding the present invention indicate that the process of bone repair can be improved by introducing insoluble bone gelatin (ISBG) into a site of the operation, for example, for impaction bone grafting.

The invention is now described with reference to the following Example.

EXAMPLE

Classifying and Grouping Donated Bone

The donors of human bones were screened and tested to determine suitability for human transplant according to international standards (e.g., American Association of Tissue Banks, European Association of Tissue Banks, Therapeutic Goods Administration of Australia).

Preparation of Bone Powder

Bone powder with a particle size of up to 1.0 millimeter was produced with a bone mill. Bone powder was collected in a sterile container and rinsed thoroughly with sterile normal saline at 50° C. to remove as much as possible blood, fat and bone marrow. Important aspects of using a fine particle size of the bone powder include enabling the success of further purification procedure for ISBG and the ability to produce an injectable form of ISBG.

Isolation and Purification of ISBG

After bone powder was prepared as described above, the bone powder was then treated sequentially as follows:

Step 1 0.6 N HCl up to 24 hr;
Step 2 2.0 M $CaCl_2$ up to 24 hr; and
Step 3 0.5 M EDTA for 4 hr.

The above steps were carried out at 0° C.-4° C. and the bone powder was rinsed twice with sterilized double distilled water each time the solution was changed. In a final step, the gelatin was treated with sterilized $H_2O$ for 4 hr at 55° C.

In one embodiment, the ISBG materials were then maintained below −70° C. to be used for further assessments such as osteoinductivity and mechanical stability.

Assessment of Osteoinductive Activity of ISBG

Rat models were used to assess the biological activities of each ISBG material produced according to the present invention. The so called attribute of osteoinductivity was assessed by introducing ISBG produced according to the present invention into two rat models. In test groups, ISBG was implanted into the tibialis anterior (TA) muscle or under skin of anterior abdominal wall of the animals. In the TA model, the skin over the TA muscle was cut to expose the muscle and the TA muscle was then cut longitudinally half way through the muscle. ISBG prepared according to the present invention was then implanted into the site and the muscle closed by suturing the cut muscle with silk sutures. The skin was then sutured using silk thread and the animal was left to recover.

In the abdominal wall model, the skin over the anterior abdominal wall was opened and the ISBG produced according to the present invention was implanted into the pocket. The skin was then closed by suturing the cut skin with silk thread and the animal left to recover. A control group was produced using the same procedures, expect bone powder was implanted rather than ISBG produced according to the present invention.

Samples were then taken 3 weeks post operatively and histopathological tests were carried out to identify scientific evidence of new bone formation induced by the bone gelatin.

It was discovered new bone appeared in the muscle where the ISBG was implanted but not in the control group where bone powder was implanted. The different results obtained using ISBG versus using bone powder clearly indicated that bone formation in the muscle was induced by the bone gelatin produced according to the present invention. To our knowledge, we are the first and the only group indicating that ISBG may be used in impaction bone grafting. The ISBG material produced by the present invention has potent osteoinductivity and mechanical stability so that we indicate that it can be used in impaction bone grafting.

Characteristics and advantages of the present invention covered in this document have been set forth in the foregoing description. It will be understood, however, that this disclosure is in many respects, only illustrative. Modifications may be made in details, particularly as to concentrations, volumes and weights of materials, and duration and ordering of steps without exceeding the scope of the present invention.

What is claimed is:

1. A process for isolating insoluble bone gelatin from bone tissue, the process comprising the steps of:
   (a) grinding the bone tissue into bone powder;
   (b) washing the bone powder with saline at 35° C. to 55° C.;
   (c) demineralizing the bone powder of step (b);
   (d) contacting the demineralized bone powder with a neutral salt to form insoluble bone gelatin; and
   (e) contacting the insoluble bone gelatin with a stabilizer, wherein said insoluble bone gelatin is thereby isolated and wherein said bone powder is not treated or contacted with organic solvents before demineralization.

2. The process of claim 1, further comprising step (f), wherein the insoluble bone gelatin is contacted with water.

3. The process of claim 1, further comprising the step of screening the bone powder before the step of demineralizing to determine the suitability of the bone tissue for transplantation.

4. The process of claim 1, wherein the bone powder comprises particles having a diameter up to 1.0 millimetres.

5. The process of claim 1, wherein the bone tissue is human bone tissue.

6. The process of claim 1, wherein the step of demineralizing the bone powder comprises contacting the bone powder with an acid.

7. The process of claim 6, wherein the acid comprises one or more acids selected from the group consisting of acetic acid and hydrochloric acid.

8. The process of claim 1, wherein the neutral salt comprises a salt selected from the group consisting of calcium chloride and calcium phosphate.

9. The process of claim 1, wherein the stabilizer comprises EDTA.

10. A process for isolating insoluble bone gelatin from bone tissue, the process comprising the steps of:
    (a) grinding the bone tissue into bone powder;
    (b) washing the bone powder with saline at between 40° C. and 45° C.;
    (c) demineralizing the bone powder of step (b);
    (d) contacting the demineralized bone powder with a neutral salt to form insoluble bone gelatin; and
    (e) contacting the insoluble bone gelatin with a stabilizer, wherein said insoluble bone gelatin is thereby isolated and wherein said bone powder is not treated or contacted with organic solvents before demineralization.

11. A method for preparing an impaction bone graft, said method comprising combining milled bone and insoluble bone gelatin, wherein said insoluble bone gelatin is isolated by a process comprising:
    (a) grinding the bone tissue into bone powder;
    (b) washing the bone powder with saline at 35° C. to 55° C.;
    (c) demineralizing the bone powder of step (b);
    (d) contacting the demineralized bone powder with a neutral salt to form insoluble bone gelatin; and
    (e) contacting the insoluble bone gelatin with a stabilizer, wherein said insoluble bone gelatin is thereby isolated and wherein said bone powder is not treated or contacted with organic solvents before demineralization.

12. The method of claim 11, wherein said demineralizing step comprises contacting the bone powder with an acid.

13. The method of claim 11, wherein said neutral salt is selected from the group consisting of calcium phosphate and calcium chloride.

14. The method of claim 11, wherein said stabilizer is EDTA.

15. An impaction bone graft formed by combining milled bone and insoluble bone gelatin isolated by the process of claim 1, wherein said insoluble bone gelatin comprises one or more growth factor(s).

16. The impaction bone graft of claim 15, wherein said one or more growth factors are selected from the group consisting of BMP-2, FGF, TGF-beta, IGF, and combinations thereof.

* * * * *